(12) United States Patent
Le Grand et al.

(10) Patent No.: US 11,589,664 B2
(45) Date of Patent: Feb. 28, 2023

(54) APPARATUS FOR PRODUCING A COSMETIC

(71) Applicants: SEB S.A., Ecully (FR); LABORATOIRES M&L, Manosque (FR)

(72) Inventors: Olivier Le Grand, Messigny et Vantoux (FR); Philippe De Brugiere, Marly le Roi (FR)

(73) Assignees: SEB S.A., Ecully (FR); DUOLAB INTERNATIONAL SARL, Plan-les-Ouates (CH)

( * ) Notice: Subject to any disclaimer, the term of this patent is extended or adjusted under 35 U.S.C. 154(b) by 383 days.

(21) Appl. No.: 16/622,147

(22) PCT Filed: Jun. 12, 2018

(86) PCT No.: PCT/FR2018/051379
§ 371 (c)(1),
(2) Date: Dec. 12, 2019

(87) PCT Pub. No.: WO2018/234658
PCT Pub. Date: Dec. 27, 2018

(65) Prior Publication Data
US 2020/0121055 A1    Apr. 23, 2020

(30) Foreign Application Priority Data

Jun. 23, 2017 (FR) ..................... 17/55744

(51) Int. Cl.
*A45D 34/00* (2006.01)
*B01F 35/92* (2022.01)
(Continued)

(52) U.S. Cl.
CPC .......... *A45D 34/00* (2013.01); *B01F 35/7131* (2022.01); *B01F 35/92* (2022.01);
(Continued)

(58) Field of Classification Search
CPC .. A61K 2800/87; A45D 40/265; A45D 34/00; A45D 2200/058; B01F 35/7131;
(Continued)

(56) References Cited

U.S. PATENT DOCUMENTS 5,246,142 A * 9/1993 DiPalma .............. B65D 25/087
222/129
2004/0195120 A1* 10/2004 Anderson .......... B65D 81/3222
206/219
(Continued)

FOREIGN PATENT DOCUMENTS

DE     9017592 A1    5/1991
FR     3026622 A1    4/2016

OTHER PUBLICATIONS

International Search Report for Application No. PCT/FR2018/051379.
(Continued)

*Primary Examiner* — Eisa B Elhilo
(74) *Attorney, Agent, or Firm* — Cantor Colburn LLP (57) ABSTRACT

The manufacturing apparatus comprises a first capsule containing a predetermined amount of a first formulation, the first capsule including a first connection portion and an outlet passage provided with an outlet orifice; a second capsule containing a predetermined amount of a second formulation, and including a second connection portion configured to be connected to the first connection portion; and a mixing machine configured to receive the first and second capsules, and to mix the first and second formulations contained in the first and second capsules so as to obtain the cosmetic product. The manufacturing apparatus is configured to automatically close the outlet passage when the first and second capsules are received in the mixing machine, and to automatically clear the outlet passage when
(Continued)

the first and second capsules are removed out of the mixing machine.

21 Claims, 6 Drawing Sheets

(51) Int. Cl.
  *B01F 35/71* (2022.01)
  *B01F 35/90* (2022.01)
  *B01F 101/21* (2022.01)

(52) U.S. Cl.
  CPC .... *A45D 2200/058* (2013.01); *A61K 2800/87* (2013.01); *B01F 2035/99* (2022.01); *B01F 2101/21* (2022.01)

(58) Field of Classification Search
  CPC ... B01F 35/92; B01F 2101/21; B01F 2035/99
  USPC ........................................................ 206/219
  See application file for complete search history.

(56) References Cited

U.S. PATENT DOCUMENTS

2014/0027322 A1* 1/2014 Fontana ............. B65D 51/2821
  206/219
2017/0304789 A1* 10/2017 Tourel .................... A45D 34/00

OTHER PUBLICATIONS

Written Opinion for Application No. PCT/FR2018/051379.
English Machine Translation of DE9017592.

\* cited by examiner

APPARATUS FOR PRODUCING A COSMETIC

CROSS REFERENCE TO RELATED APPLICATIONS

This application is a National Stage of PCT Application No. PCT/FR2018/051379 filed on Jun. 12, 2018, which claims priority to French Patent Application No. 17/55744 filed on Jun. 23, 2017, the contents each of which are incorporated herein by reference thereto.

TECHNICAL FIELD

The present invention concerns an apparatus for manufacturing a cosmetic product.

BACKGROUND

FR3026622 discloses an apparatus for manufacturing a cosmetic product, including:
a first capsule containing a predetermined amount of a first formulation, the first capsule including a first connection portion and an outlet passage provided with an outlet orifice,
a second capsule containing a predetermined amount of a second formulation, and including a second connection portion configured to be connected to the first connection portion, and
a mixing machine configured to:
receive the first and second capsules,
close the outlet passage,
mix the first and second formulations inside the first and second capsules so as to obtain the cosmetic product, and
clear the outlet passage so as to subsequently enable the discharge of the manufactured cosmetic product out of the first capsule and the recovery of the manufactured cosmetic product on a receiving cup.

In particular, such a mixing machine includes a closure element displaceable between a position for closing the outlet passage and a position for clearing the outlet passage, and a control unit configured to control the displacements of the closure element between the closing and clearance positions.

Such a manufacturing apparatus enables the manufacture, by an end consumer, of a customized cosmetic product from different capsules.

However, the structure of the manufacturing apparatus described in FR3026622 may be simplified further. In addition, the use of the manufacturing apparatus described in FR3026622 may turn out to be complex for some consumers, in particular when it is necessary to perform a connection of the first and second capsules prior to their insertion into the mixing machine.

The present invention aims at overcoming all or part of these drawbacks.

BRIEF SUMMARY

The technical problem at the origin of the invention consists therefore in providing an apparatus for manufacturing a cosmetic product which is simple and easy to use, while having a simple and reliable structure.

To this end, the present invention concerns an apparatus for manufacturing a cosmetic product, comprising:
a first capsule containing a predetermined amount of a first formulation, the first capsule including a first connection portion and an outlet passage provided with an outlet orifice,
a second capsule containing a predetermined amount of a second formulation, and including a second connection portion configured to be connected to the first connection portion,
a mixing machine configured to receive the first and second capsules, preferably fluidly connected to each other by the first and second connection portions, and to mix the first and second formulations contained in the first and second capsules so as to obtain the cosmetic product,
characterized in that the outlet passage is fluidly connected to the first connection portion, and in that the manufacturing apparatus is configured to automatically close the outlet passage when the first and second capsules are received in the mixing machine, and to automatically clear the outlet passage when the first and second capsules are removed out of the mixing machine.

Such a configuration of the manufacturing apparatus, and in particular the automatic closing of the outlet passage upon the reception of the first and second capsules in the mixing machine, ensures a simple and reliable closing of the outlet passage, and in particular during the mixture of the first and second formulations.

In addition, the automatic clearance of the outlet passage, upon the removal of the first and second capsules out of the mixing machine, ensures a simple and reliable clearance of the outlet passage, without requiring the control of a particular actuator.

Thus, the manufacturing apparatus according to the present invention has a simple and reliable structure, while being simple and easy to use.

In the present invention, by «fluidly connected» is meant the fact that a fluidic communication can be established between the different elements associated to the expression «fluidly connected».

The manufacturing apparatus may further present one or more of the following features, considered separately or in combination.

According to an embodiment of the invention, the manufacturing apparatus is configured to automatically close the outlet passage concomitantly with the insertion of the first and second capsules into the mixing machine, and to automatically clear the outlet passage concomitantly with the removal of the first and second capsules out of the mixing machine.

According to an embodiment of the invention, the manufacturing apparatus further includes a receiving device configured to receive the first and second capsules, the mixing machine being configured to receive the receiving device equipped with the first and second capsules.

According to an embodiment of the invention, the receiving device is capable of occupying an open position in which the first and second capsules can be introduced into the receiving device, and a closed position in which the receiving device can hold the first and second capsules in position.

According to an embodiment of the invention, the receiving device is configured to fluidly connect the first and second connection portions when the receiving device is displaced into the closed position.

According to an embodiment of the invention, the receiving device includes a receiving case configured to receive and house at least partially the first and second capsules.

Advantageously, the manufacturing apparatus is configured to automatically close the outlet passage when the receiving device equipped with the first and second capsules is received in the mixing machine, and to automatically clear the outlet passage when the receiving device is removed out of the mixing machine.

According to an embodiment of the invention, the first capsule includes a first deformable compartment containing the first formulation, and the second capsule includes a second deformable compartment containing the second formulation.

According to an embodiment of the invention, the first capsule further includes a first connecting passage configured to fluidly connect the first deformable compartment and the first connection portion, and the second capsule further includes a second connecting passage configured to fluidly connect the second deformable compartment and the second connection portion.

According to an embodiment of the invention, the outlet passage is fluidly connected to the first connecting passage. For example, the outlet passage may open into the first connecting passage.

According to an embodiment of the invention, the outlet passage extends in the extension of the first connecting passage.

Advantageously, the outlet passage extends substantially parallel to the first connecting passage.

According to an embodiment of the invention, the first connection portion extends substantially perpendicular with respect to the first connecting passage.

According to an embodiment of the invention, the manufacturing apparatus includes a closure element configured to automatically close the outlet passage when the first and second capsules are received in the mixing machine, for example when the receiving device equipped with the first and second capsules is received in the mixing machine, and to automatically clear the outlet passage when the first and second capsules are removed out of the mixing machine, and for example when the receiving device equipped with the first and second capsules is removed out of the mixing machine.

According to an embodiment of the invention, the closure element is configured to pinch the outlet passage or to exert a pressure on the outlet passage.

According to an embodiment of the invention, the closure element is movably mounted between a closing position in which the closure element is capable of closing the outlet passage, and for example capable of pinching the outlet passage or exerting a pressure on the outlet passage, and a clearance position in which the closure element is capable of clearing the outlet passage.

According to an embodiment of the invention, the mixing machine includes a displacement element configured to displace the closure element into the closing position when the first and second capsules are received in the mixing machine, and for example when the receiving device is inserted into the mixing machine.

According to an embodiment of the invention, the manufacturing apparatus is configured such that the introduction of the receiving device into the mixing machine up to an abutment position of the receiving device mechanically causes a displacement of the closure element into the closing position. In particular, these arrangements allow avoiding the presence of an end-of-travel detector, and of an actuator coupled to the end-of-travel detector and capable of displacing the closure element into the closing position.

According to an embodiment of the invention, the manufacturing apparatus is configured such that the removal of the receiving device out of the mixing machine mechanically causes a displacement of the closure element into the clearance position.

According to an embodiment of the invention, the manufacturing apparatus includes a counter-support element configured to bear against the first capsule and to be disposed opposite the closure element when the first and second capsules are received in the mixing machine, and for example when the receiving device equipped with the first and second capsules is received in the mixing machine.

Advantageously, the counter-support element is configured to be disposed opposite the closure element when the receiving device is in the closed position.

According to an embodiment of the invention, the receiving device includes the counter-support element.

According to an embodiment of the invention, the first connecting passage is a first connecting channel, and the second connecting passage is a second connecting channel.

According to an embodiment of the invention, the outlet passage is an outlet channel.

According to an embodiment of the invention, each of the first and second capsules is intended for a single use.

According to an embodiment of the invention, the receiving device includes the closure element.

According to an embodiment of the invention, the first capsule includes a thermoformed shell and a sealing sheet covering the thermoformed shell, the thermoformed shell and the sealing sheet of the first capsule delimiting the outlet passage.

According to an embodiment of the invention, the second capsule also includes a thermoformed shell and a sealing sheet covering the respective thermoformed shell, the thermoformed shell and the sealing sheet of the first capsule delimiting the first deformable compartment and the first connecting passage, and the thermoformed shell and the sealing sheet of the second capsule delimiting the second deformable compartment and the second connecting passage.

According to an embodiment of the invention, the mixing machine is configured to mix the first and second formulations inside the first and second capsules. Such a configuration allows at least avoiding a contact between the mixing machine and the first and second formulations, and therefore avoiding a subsequent cleaning of the mixing machine after the manufacture of the cosmetic product.

According to an embodiment of the invention, the manufacturing apparatus includes a heating element configured to heat up at least one of the first and second capsules when the first and second capsules are received in the mixing machine, and for example when the receiving device equipped with the first and second capsules is received in the mixing machine.

According to an embodiment of the invention, the heating element is configured to heat up the first capsule. Advantageously, the heating element is configured to extend along an external surface of the first capsule.

According to an embodiment of the invention, the heating element is disposed in the receiving device or in the mixing machine.

According to an embodiment of the invention, the heating element is configured to extend between the first and second capsules.

According to an embodiment of the invention, the heating element is disposed in the mixing machine and is configured to extend between the first and second capsules when the receiving device equipped with the first and second capsules is received in the mixing machine.

According to another embodiment of the invention, the heating element is disposed in the receiving device and is configured to extend between the first and second capsules when the first and second capsules are received in the receiving device.

According to an embodiment of the invention, the manufacturing apparatus includes a first actuation member configured to transmit a pressing force to the first capsule, and a second actuation member configured to transmit a pressing force to the second capsule. For example, the mixing machine includes the first and second actuation members.

According to another embodiment of the invention, the first actuation member is configured to transmit a pressing force to the first capsule so as to make the content of the first capsule migrate into the second capsule, and the second actuation member is configured to transmit a pressing force to the second capsule so as to make the content of the second capsule migrate into the first capsule.

According to an embodiment of the invention, the first and second actuation members are configured to alternately transmit pressing forces respectively to the first and second capsules.

According to an embodiment of the invention, the first and second actuation members are disposed opposite each other.

According to another embodiment of the invention, the first and second actuation members are configured to be disposed on either side of the receiving device when the receiving device is received in the mixing machine.

According to another embodiment of the invention, the mixing machine includes:
  an actuation portion including the first and second actuation members, the actuation portion being pivotally mounted about a pivot axis, and
  a drive motor configured to make the actuation portion pivot about the pivot axis and alternately in a first pivot direction and in a second pivot direction opposite to the first pivot direction.

According to an embodiment of the invention, the drive motor is configured to make the actuation portion pivot about the pivot axis and within a predetermined angular range.

According to an embodiment of the invention, the first and second actuation members converge opposite to the pivot axis.

According to an embodiment of the invention, the mixing machine is configured such that a rotation of the drive motor in a first direction of rotation causes a pivoting of the actuation portion in the first pivot direction and a rotation of the drive motor in a second direction of rotation, opposite to the first direction of rotation, causes a pivoting of the actuation portion in the second pivot direction.

According to another embodiment of the invention, the mixing machine further includes a drive wheel rotatably secured to an output shaft of the drive motor and configured to be driven in rotation about its wheel axis by the drive motor, the drive wheel being equipped with a drive element, such as a drive pin, eccentric with respect to the wheel axis, and the actuation portion includes a receiving aperture which is elongate and in which the drive element is received.

According to an embodiment of the invention, the receiving aperture extends according to a direction of extension substantially parallel to the pivot axis.

According to an embodiment of the invention, the receiving device is configured such that, when the receiving device equipped with the first and second capsules is in the closed position, an orthogonal projection of the first capsule on a reference plane is at least partially coincident with an orthogonal projection of the second capsule on the reference plane. Advantageously, the receiving device is configured such that, when the receiving device equipped with the first and second capsules is in the closed position, an orthogonal projection of the first deformable compartment of the first capsule on a reference plane is at least partially coincident with an orthogonal projection of the second deformable compartment of the second capsule on the reference plane.

According to an embodiment of the invention, the receiving device is configured such that the first and second capsules extend substantially parallel to each other when the receiving device equipped with the first and second capsules is in the closed position.

According to an embodiment of the invention, the receiving device includes a locking element configured to lock the receiving device in the closed position.

According to an embodiment of the invention, the locking element is movable between a locking position in which the locking element locks the receiving device in the closed position, and an unlocking position in which the locking element enables a displacement of the receiving device into the open position.

According to an embodiment of the invention, the receiving device includes a release element, such as a release button, configured to displace the locking element into the unlocking position.

According to an embodiment of the invention, the first connection portion includes a male connection fitting, for example cylindrical, and the second connection portion includes a female connection fitting, for example cylindrical, configured to receive the male connection fitting.

According to an embodiment of the invention, the receiving device includes a first protecting shell and a second protecting shell movably mounted relative to each other between a first position corresponding to an open position of the receiving device and a second position corresponding to a closed position of the receiving device.

For example, the first and second protecting shells are hingedly mounted relative to each other about a hinge axis.

Advantageously, the closure element is movably mounted on the first protecting shell.

Advantageously, the counter-support element is provided on the second protecting shell.

According to an embodiment of the invention, the receiving device includes a first receiving location configured to receive the first capsule and a second receiving location configured to receive the second capsule.

According to an embodiment of the invention, the receiving device includes a first support portion including the first receiving location and a second support portion including the second receiving location, the first and second support portions being movable relative to each other between a receiving position in which the first and second support portions are brought away from each other and the first and second capsules can be received respectively in the first and second receiving locations, and a connection position in which the first and second support portions are brought close to each other and the first and second capsules can be connected to each other.

According to an embodiment of the invention, the first and second support portions are configured to be displaced into the connection position when the receiving device is displaced into the closed position.

According to an embodiment of the invention, the first and second support portions are hingedly mounted relative to each other about a hinge axis.

According to an embodiment of the invention, the first and second protecting shells and the first and second support portions are hingedly mounted about the same hinge axis.

According to an embodiment of the invention, the first receiving location includes a first receiving groove configured to receive at least one portion of the first capsule, and the second receiving location includes a second receiving groove configured to receive at least one portion of the second capsule. Advantageously, each of the first and second receiving grooves is substantially arcuate. Advantageously, each of the first and second receiving grooves is configured to cooperate with a peripheral edge of the respective one of the first and second capsules.

According to an embodiment of the invention, the first support portion includes a first fault-proof element, such as a first fault-proof notch, configured to cooperate with the first connection portion, and the second support portion includes a second fault-proof element, such as a second fault-proof notch, configured to cooperate with the second connection portion.

According to an embodiment of the invention, the mixing machine includes a receiving housing configured to receive the first and second capsules, and for example to receive at least partially the receiving device equipped with the first and second capsules.

According to an embodiment of the invention, the mixing machine includes an insertion opening leading into the receiving housing, the first and second capsules being configured to be inserted into the receiving housing through the insertion opening. Advantageously, the receiving device, equipped with the first and second capsules, is configured to be inserted into the receiving housing through the insertion opening. Advantageously, the insertion opening is configured to be orientated upwardly when the mixing machine is disposed on a planar support.

According to an embodiment of the invention, the mixing machine and the receiving device are configured such that the receiving device extends at least partially outside the mixing machine when the receiving device is received in the receiving housing.

According to an embodiment of the invention, the mixing machine includes a base having an upper surface on which the insertion opening is formed.

According to an embodiment of the invention, the receiving housing is located in a central area of the base.

According to an embodiment of the invention, the mixing machine includes an electric power supply source configured to electrically power the mixing machine. Advantageously, the electric power supply source includes at least one rechargeable battery.

According to an embodiment of the invention, the electric power supply source is configured to electrically power the receiving device when the receiving device is received in the mixing machine.

According to an embodiment of the invention, the mixing machine includes a first electrical connector, and the receiving device includes a second electrical connector configured to be connected to the first electrical connector when the receiving device is received in the mixing machine, so that the mixing machine is capable of electrically powering the receiving device.

According to an embodiment of the invention, the manufacturing apparatus comprises a controller configured to control the drive motor and/or the heating element.

According to an embodiment of the invention, the heating element is configured to heat up the first deformable compartment. Advantageously, the heating element is configured to extend proximate to the first deformable compartment, and preferably adjacent to the first deformable compartment.

According to an embodiment of the invention, each of the first and second capsules is configured to contain the entirety or substantially the entirety of a mixture formed by the predetermined amount of the first formulation and the predetermined amount of the second formulation.

According to an embodiment of the invention, the first formulation is a first phase of the cosmetic product, and the second formulation is a second phase of the cosmetic product.

According to an embodiment of the invention, the first formulation is a fatty phase of the cosmetic product, and the second formulation is an aqueous phase of the cosmetic product. For example, the fatty phase constitutes the base of the cosmetic product to manufacture, and the aqueous phase comprises active elements and constitutes the complex of active ingredients of the cosmetic product to manufacture.

According to an embodiment of the invention, the manufactured cosmetic product is a homogenized emulsion, a homogenized solution or a mixture of several miscible phases.

According to an embodiment of the invention, the first capsule is configured to extend at least partially outside the receiving device when it is received in the receiving device. Advantageously, the outlet orifice is configured to extend outside the receiving device when the first capsule is received in the receiving device.

According to an embodiment of the invention, the receiving device includes a first bearing element configured to exert a pressing force on the first capsule, and for example on the first deformable compartment, when the receiving device is equipped with the first and second capsules, and a second bearing element configured to exert a pressing force on the second capsule, and for example on the second deformable compartment, when the receiving device is equipped with the first and second capsules.

According to an embodiment of the invention, the first bearing element extends through a first passage opening provided on the first protecting shell, and the second bearing element extends through a second passage opening provided on the second protecting shell.

According to an embodiment of the invention, the first actuation member is configured to transmit a pressing force to the first bearing element, and the second actuation member is configured to transmit a pressing force to the second bearing element.

According to an embodiment of the invention, the first bearing element is movable and/or deformable between an inactive position and an active positon in which the first bearing element is capable of exerting a pressing force on the first capsule, and the second bearing element is movable and/or deformable between an inactive position and an active position in which the second bearing element is capable of exerting a pressing force on the second capsule. For example, each of the first and second bearing elements is mounted movable in translation, for example along a direction of displacement which is transverse, and preferably substantially orthogonal, to the planes of extension of the first and second capsules when the first and second capsules are received in the mixing machine.

Advantageously, the inactive position of the first bearing element corresponds to a position of the first bearing element in which, when the receiving device is equipped with the first and second capsules:

the first bearing element is located at a distance from the first capsule, and more particularly from the first deformable compartment, or the first bearing element is only in contact with the first capsule, and more particularly with the first deformable compartment, or the first bearing element exerts a pressing force on the first capsule, and more particularly on the first deformable compartment, which is insufficient to make the content of the first deformable compartment migrate toward the second capsule.

Advantageously, the inactive position of the second bearing element corresponds to a position of the second bearing element in which, when the receiving device is equipped with the first and second capsules:

the second bearing element is located at a distance from the second capsule, and more particularly from the second deformable compartment, or the second bearing element is only in contact with the second capsule, and more particularly with the second deformable compartment, or the second bearing element exerts a pressing force on the second capsule, and more particularly on the second deformable compartment, which is insufficient to make the content of the second deformable compartment migrate toward the first capsule.

Advantageously, the active position of the first bearing element corresponds to a position of the first bearing element in which, when the receiving device is equipped with the first and second capsules, the first bearing element exerts a pressing force on the first capsule, and more particularly on the first deformable compartment, which is sufficient to make the content of the first deformable compartment migrate toward the second capsule, and the active position of the second bearing element corresponds to a position of the second bearing element in which, when the receiving device is equipped with the first and second capsules, the second bearing element exerts a pressing force on the second capsule, and more particularly on the second deformable compartment, which is sufficient to make the content of the second deformable compartment migrate toward the first capsule.

According to an embodiment of the invention, the first and second bearing elements are mounted respectively on the first and second protecting shells.

According to an embodiment of the invention, the first bearing element includes a first bearing surface configured to cooperate with the first capsule, and for example with the first deformable compartment, the first bearing surface being configured to guide and orientate the content of the first capsule toward the first connection portion when the first bearing element exerts a pressing force on the first capsule, and the second bearing element includes a second bearing surface configured to cooperate with the second capsule, and for example with the second deformable compartment, the second bearing surface being configured to guide and orientate the content of the second capsule toward the second connection portion when the second bearing element exerts a pressing force on the second capsule.

According to an embodiment of the invention, when the first bearing element is displaced from the inactive position toward the active position, the first bearing surface is configured to exert a bearing force successively on a first portion of the first deformable compartment located at a first primary distance from the first connecting passage and on a second portion of the first deformable compartment located at a second primary distance from the first connecting passage, the second primary distance being smaller than the first primary distance, and wherein, when the second bearing element is displaced from the inactive position toward the active position, the second bearing surface is configured to exert a bearing force successively on a first portion of the second deformable compartment located at a first secondary distance from the second connecting passage and on a second portion of the second deformable compartment located at a second secondary distance from the second connecting passage, the second secondary distance being smaller than the first secondary distance.

According to an embodiment of the invention, the first bearing surface includes a first primary surface portion configured to exert a pressing force on the first portion of the first deformable compartment, and a second primary surface portion configured to exert a pressing force on the second portion of the first deformable compartment, and the second bearing surface includes a first secondary surface portion configured to exert a pressing force on the first portion of the second deformable compartment, and a second secondary surface portion configured to exert a pressing force on the second portion of the second deformable compartment.

According to an embodiment of the invention, the first and second primary surface portions are configured such that, when the first bearing element is displaced and/or deformed in the active position, the first primary surface portion exerts a pressing force on the first capsule before the second primary surface portion exerting a pressing fore on the first capsule.

Advantageously, the first and second primary surface portions are configured to respectively exert a pressing force on rear and front portions of the first deformable compartment.

According to an embodiment of the invention, the first and second secondary surface portions are configured such that, when the second bearing element is displaced and/or deformed in the active position, the first secondary surface portion exerts a pressing force on the second capsule before the second secondary surface portion exerting a pressing force on the second capsule.

Advantageously, the first and second secondary surface portions are configured to respectively exert a pressing force on rear and front portions of the second deformable compartment.

According to an embodiment of the invention, the first bearing element includes a first actuation surface opposite to the first bearing surface, and the second bearing element includes a second actuation surface opposite to the second bearing surface, the first and second actuation members being configured to exert pressing forces respectively on the first and second actuation surfaces. Advantageously, each of the first and second actuation surfaces is accessible from the outside of the receiving device.

According to an embodiment of the invention, the receiving device includes at least one primary guide element, such as a guide groove, configured to cooperate with at least one secondary guide element, such as a guide pin, provided on the mixing machine, when the receiving device is received in the mixing machine.

According to an embodiment of the invention, the manufacturing apparatus is configured such that the introduction of the receiving device into the mixing machine mechanically and automatically causes the closing of the outlet passage.

The present invention further concerns an apparatus for manufacturing a cosmetic product, comprising:

a first capsule including a first compartment containing a predetermined amount of a first formulation, a second capsule including a second compartment containing a predetermined amount of a second formulation, the first and second capsules being distinct from each other, a communication passage configured to fluidly connect the first and second compartments of the first and second capsules, and a mixing machine configured to receive the first and second capsules fluidly connected by the communication passage, and to mix the first and second formulations contained in the first and second compartments so as to obtain the cosmetic product, characterized in that the manufacturing apparatus further includes an outlet passage fluidly connected to the communication passage and provided with an outlet orifice, and in that the manufacturing apparatus is configured to automatically close the outlet passage when the first and second capsules are received in the mixing machine, and to automatically clear the outlet passage when the first and second capsules are removed out of the mixing machine.

According to an embodiment of the invention, the first capsule includes a first connection portion, and the second capsule includes a second connection portion configured to be connected to the first connection portion, the communication passage being formed at least partially by the first and second connection portions.

According to an embodiment of the invention, the first capsule further includes a first connecting passage configured to fluidly connect the first deformable compartment and the first connection portion, and the second capsule further includes a second connecting passage configured to fluidly connect the second deformable compartment and the second connection portion, the communication passage being further formed at least partially by the first and second connecting passages.

The present invention also concerns a method for manufacturing a cosmetic product, comprising the following steps of:

providing a manufacturing apparatus according to the invention, manually inserting the first and second capsules into the mixing machine, automatically closing the outlet passage, mixing the first and second formulations so as to obtain the cosmetic product, manually removing the first and second capsules out of the mixing machine, and automatically clearing the outlet passage.

According to an implementation of the manufacturing method, the insertion and closing steps are concomitant.

According to an implementation of the manufacturing method, the latter further comprises the following steps of:

removing the first and second capsules out of the mixing machine, and automatically clearing the outlet passage.

According to an implementation of the manufacturing method, the removal and clearance steps are concomitant.

BRIEF DESCRIPTION OF THE DRAWINGS

Anyway, the invention will be better understood from the following description with reference to the appended schematic drawings representing, as non-limiting examples, several embodiments of this manufacturing apparatus.

DETAILED DESCRIPTION

FIGS. 1 to 22 represent a manufacturing apparatus 2, according to a first embodiment of the invention, configured to manufacture a cosmetic product, which may be for example a homogenized emulsion, a homogenized solution or still a mixture of several miscible phases.

Figure 1:
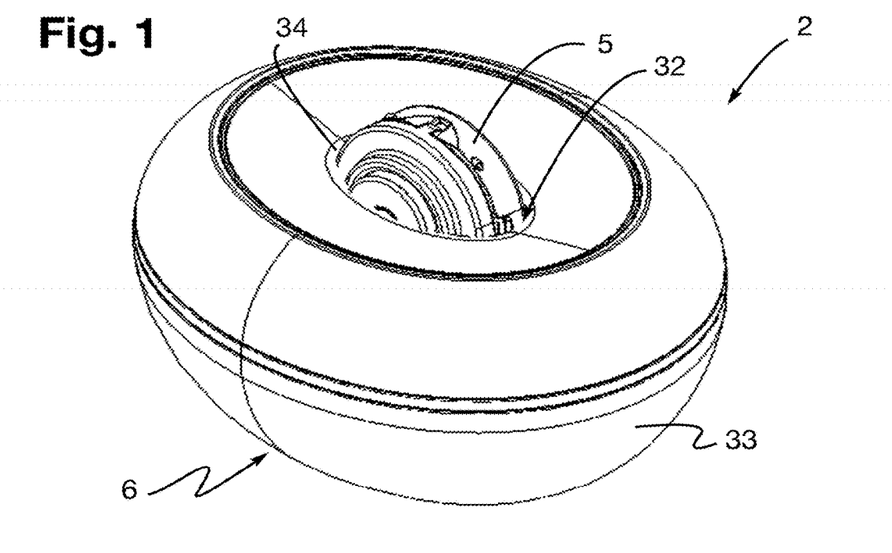
FIG. 1 is a perspective view of a manufacturing apparatus according to a first embodiment of the invention.
Figure 2:
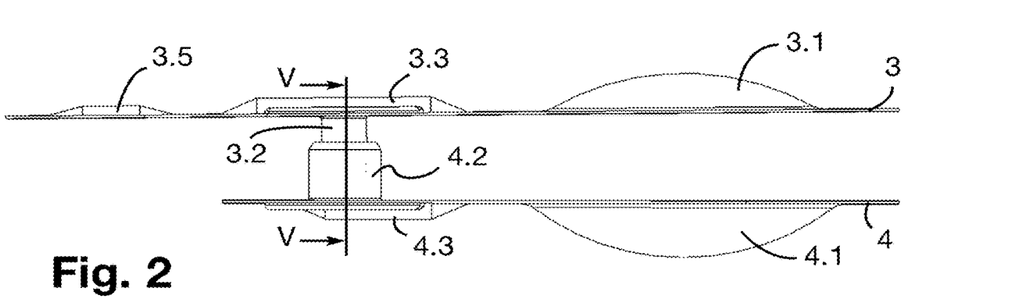
FIG. 2 is a side view of a first capsule and of a second capsule connected to each other and belonging to the manufacturing apparatus of FIG. 1.
Figure 3:
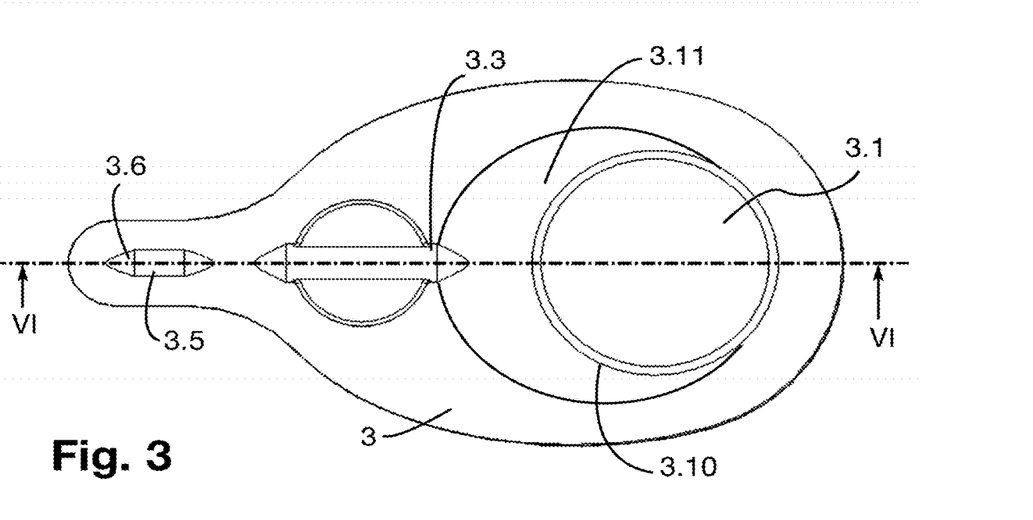
FIGS. 3 and 4 are top views respectively of the first and second capsules of FIG. 2.

In particular, the manufacturing apparatus 2 comprises first and second capsules 3, 4, also called pods or packaging units, respectively containing a predetermined amount of a first formulation and a predetermined amount of a second formulation, a receiving device 5 configured to receive the first and second capsules 3, 4, and a mixing machine 6 configured to receive the receiving device 5 equipped with the first and second capsules 3, 4, and to mix the first and second formulations contained in the first and second capsules 3, 4 so as to obtain a cosmetic product. Advantageously, the mixing machine 6 is configured to mix the first and second formulations inside the receiving device 5, and preferably inside the first and second capsules 3, 4.

Advantageously, the first formulation is a first phase of the cosmetic product to manufacture, such as a fatty phase of the cosmetic product, whereas the second formulation is a second phase of the cosmetic product, such as an aqueous phase of the cosmetic product. For example, the fatty phase may constitute the base of the cosmetic product to manufacture, and the aqueous phase may comprise active elements and thus constitute a complex of active ingredients of the cosmetic product to manufacture.

As shown more particularly in FIGS. 2 to 6, the first and second capsules 3, 4 are distinct from each other, and are configured to be fluidly connected to each other. Furthermore, each of the first and second capsules 3, 4 is advantageously intended for a single use.

The first capsule 3 includes a first deformable compartment 3.1 containing the first formulation, a first connection portion 3.2 and a first connecting passage 3.3 configured to fluidly connect the first deformable compartment 3.1 and the first connection portion 3.2. Advantageously, the first connecting passage 3.3 is formed by a first connecting channel, and the first connection portion 3.2 extends substantially perpendicular with respect to the first connecting passage 3.3. More particularly, the first connection portion 3.2 includes a male connection fitting 3.4, for example cylindrical shaped, fluidly connected to the first connecting passage 3.3.

According to the embodiment represented in the figures, the first deformable compartment 3.1 includes a first frangible peripheral area 3.10 having one or several frangible portion(s), also called weakening portions, configured to break up when a sufficient mechanical pressure is exerted on the first deformable compartment 3.1.

Advantageously, the first capsule 3 also includes a first buffer area 3.11 extending at least partially around the first peripheral area 3.10 of the first deformable compartment 3.1, and the frangible portion(s) of the first deformable compartment 3.1 are located such that, when the frangible portion(s) are broken, the content of the first deformable compartment 3.1 can flow into the first buffer area 3.11.

More particularly, the first buffer area 3.11 is configured to fluidly connect the first deformable compartment 3.1 and the first connecting passage 3.3 when the frangible portion(s) of the first deformable compartment 3.1 are broken. Advantageously, before the breakage of the frangible portion(s) of the first deformable compartment 3.1, the two walls delimiting the first buffer area 3.11 are in contact with each other such that the volume of the first buffer area 3.11 is then substantially zero. After the breakage of the frangible portion(s) of the first deformable compartment 3.1, the flow of the content of the first deformable compartment 3.1 into the first buffer area 3.11 induces a deviation of the two walls delimiting the first buffer area 3.11, and therefore an increase of the volume of the first buffer area 3.11.

The first capsule 3 further includes an outlet passage 3.5, such as an outlet channel, which is fluidly connected to the first connecting passage 3.3, and which is provided with an outlet orifice 3.6. Advantageously, the outlet passage 3.5 extends in the extension of the first connecting passage 3.3, and substantially parallel to the first connecting passage 3.3.

According to the embodiment represented in FIGS. 1 to 22, the first capsule 3 includes a thermoformed shell 3.7 and a sealing sheet 3.8 covering the thermoformed shell 3.7. Advantageously, the thermoformed shell 3.7 and the sealing sheet 3.8 of the first capsule 3 delimit the first deformable compartment 3.1, the first connecting passage 3.3 and the outlet passage 3.5.

Figure 4:
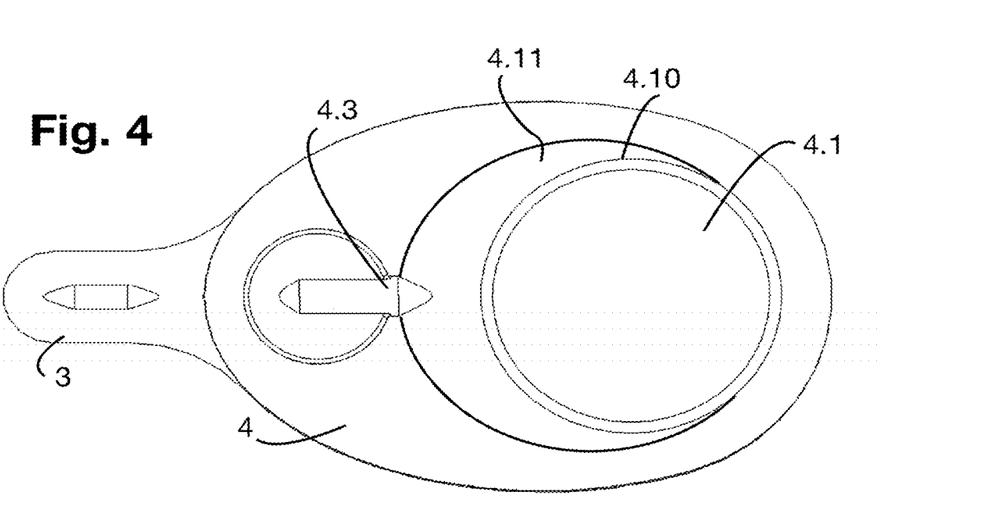
Figure 5:
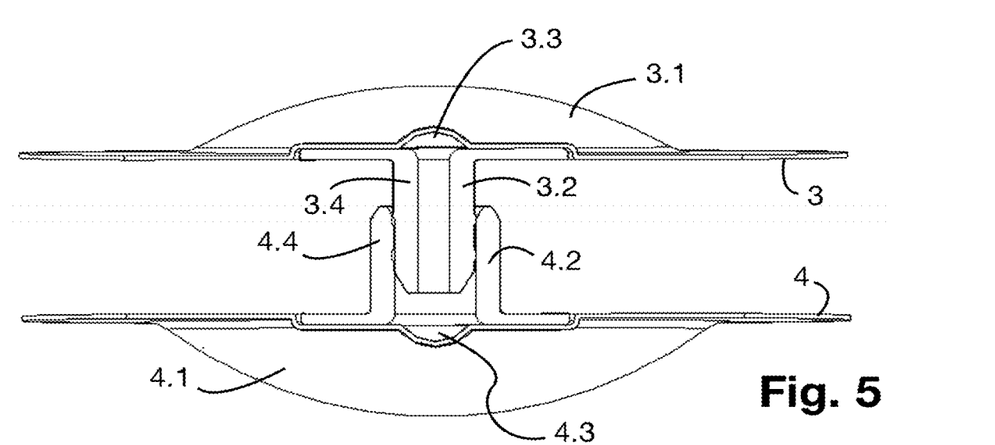
FIG. 5 is a sectional view according to line V-V of FIG. 2.
Figure 6:
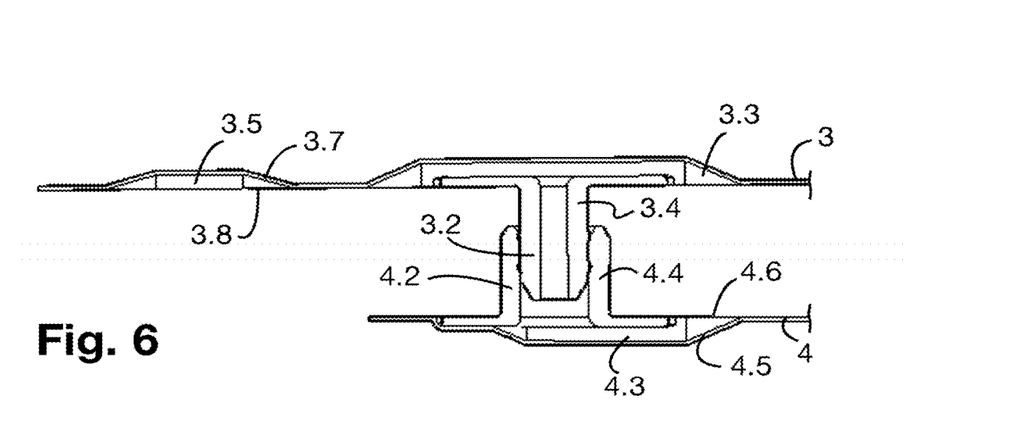
FIG. 6 is a partial sectional view according to line VI-VI of FIG. 3.

The second capsule 4 includes a second deformable compartment 4.1 containing the second formulation, a second connection portion 4.2 configured to be connected to the first connection portion 4.1, and a second connecting passage 4.3 configured to fluidly connect the second deformable compartment 4.1 and the second connection portion 4.2. Advantageously, the second connecting passage 4.3 is formed by a second connecting channel, and the second connection portion 4.2 extends substantially perpendicular with respect to the second connecting passage 4.3. More particularly, the second connection portion 4.2 includes a female connection fitting 4.4, for example cylindrical shaped, fluidly connected to the second connecting passage 4.3 and configured to tightly receive the male connection fitting 3.4.

According to the embodiment represented in the figures, the second deformable compartment 4.1 includes a second frangible peripheral area 4.10 having one or several frangible portion(s), also called weakening portions, configured to break up when a sufficient mechanical pressure is exerted on the second deformable compartment 4.1.

Advantageously, the second capsule 4 also includes a second buffer area 4.11 extending at least partially around the second peripheral area 4.10 of the second deformable compartment 4.1, and the frangible portion(s) of the second deformable compartment 4.1 are located such that, when the frangible portion(s) are broken, the content of the second deformable compartment 4.1 can flow into the second buffer area 4.11.

More particularly, the second buffer area 4.11 is configured to fluidly connect the second deformable compartment 4.1 and the second connecting passage 4.3 when the frangible portion(s) of the second deformable compartment 4.1 are broken. Advantageously, before the breakage of the frangible portion(s) of the second deformable compartment 4.1, the two walls delimiting the second buffer area 4.11 are in contact with each other such that the volume of the second buffer area 4.11 is then substantially zero.

According to the embodiment represented in FIGS. 1 to 22, the second capsule 4 includes a thermoformed shell 4.5 and a sealing sheet 4.6 covering the thermoformed shell 4.5. Advantageously, the thermoformed shell 4.5 and the sealing sheet 4.6 of the second capsule 4 delimit the second deformable compartment 4.1 and the second connecting passage 4.3.

Advantageously and for reasons set out hereinafter, each of the first and second capsules 3, 4 is configured to contain the entirety or substantially the entirety of a mixture formed by the predetermined amount of the first formulation and the predetermined amount of the second formulation.

As shown more particularly in FIGS. 7 to 14, the receiving device 5 is capable of occupying an open position in which the first and second capsules 3, 4 can be introduced into the receiving device 5, and a closed position in which the receiving device 5 is capable of holding the first and second capsules 3, 4 in position.

More particularly, the receiving device 5 includes a receiving case 7 configured to receive and house at least partially the first and second capsules 3, 4. In particular, the receiving case 7 includes a first protecting shell 8 and a second protecting shell 9 hingedly mounted relative to each other about a hinge axis 10 and between a first position (see FIG. 8) corresponding to an open position of the receiving device 5 and a second position (see FIG. 7) corresponding to a closed position of the receiving device 5. For example, the first and second protecting shells 8, 9 may have an angle of inclination comprised between 50 and 90°, and for example of about 70°, when they are in the first position.

The receiving device 5 further includes a first support portion 11 and a second support portion 12 disposed in the receiving case 7. The first and second support portions 11, 12 respectively include a first receiving location 13 configured to receive the first capsule 3 and a second receiving location 14 configured to receive the second capsule 4. Advantageously, the first receiving location 13 includes a first receiving groove 15 configured to receive a peripheral portion of the first capsule 3, and the second receiving location 14 includes a second receiving groove (not shown in the figures) configured to receive a peripheral portion of the second capsule 4.

According to the embodiment represented in FIGS. 1 to 22, the first and second support portions 11, 12 are hinged relative to each other about the hinge axis 10 and between a receiving position (see FIGS. 8 and 13) in which the first and second support portions 11, 12 are brought away from each other and the first and second capsules 3, 4 can be received respectively in the first and second receiving locations 13, 14, and a connection position (see FIG. 12) in which the first and second support portions 11, 12 are brought close to each other and the first and second capsules 3, 4 can be connected to each other. For example, the first and second support portions 11, 12 may have an angle of inclination comprised between 5 and 20°, and for example of about 10°, when they are in the receiving position, and be substantially parallel to each other when they are in the connection position.

Advantageously, the first and second support portions 11, 12 are configured to be displaced in the connection position when the receiving device 5 is displaced into the closed position, and therefore to fluidly connect the first and second connection portions 3.2, 4.2 when the receiving device 5 is displaced into the closed position.

The first support portion 11 further includes a first fault-proof element 17, such as a first fault-proof notch, configured to cooperate with the first connection portion 3.2 of the first capsule 3, and the second support portion 12 includes a second fault-proof element 18, such as a second fault-proof notch, configured to cooperate with the second connection portion 4.2. The first and second fault-proof elements 17, 18 allow ensuring a positioning of the first capsule 3 exclusively on the first support portion 11, and a positioning of the second capsule 4 exclusively on the second support portion 12, and thus avoiding any error of positioning of the first and second capsules 3, 4 in the receiving device 5.

More particularly, the first and second support portions 11, 12 are configured such that the first and second capsules 3, 4 extend substantially parallel to each other, when the first and second support portions 11, 12 are in the connection position.

Figures 7, 8:
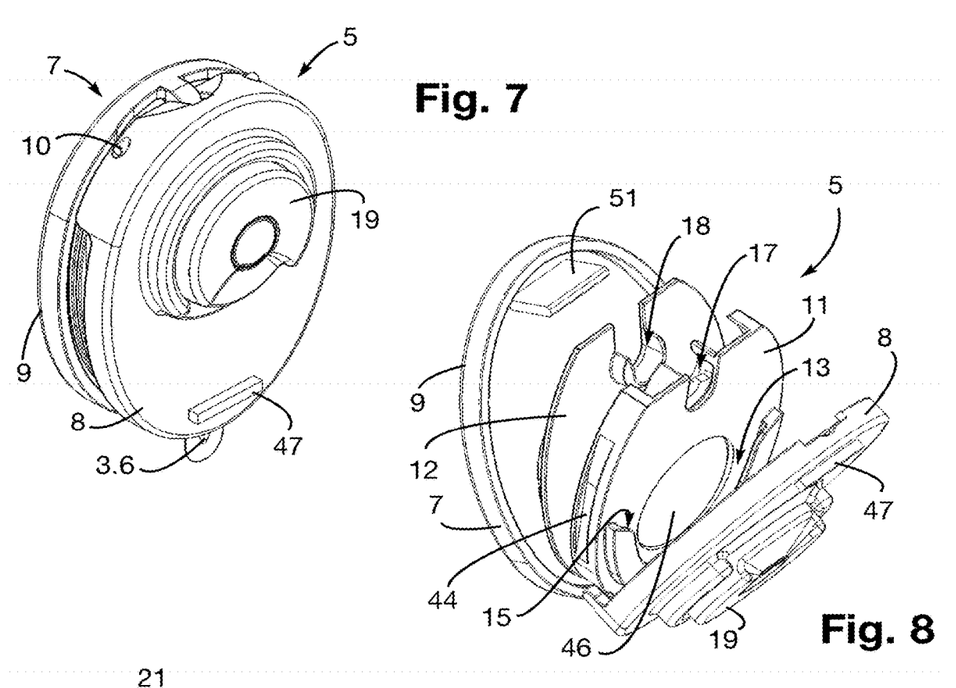
FIG. 7 is a perspective view of a receiving device belonging to the manufacturing apparatus of FIG. 1, showing the receiving device in the closed position.
FIG. 8 is a perspective view of the receiving device of FIG. 7, in the open position, the receiving device being represented in a reversed position with regards to the position illustrated in FIG. 7.
Figure 13:
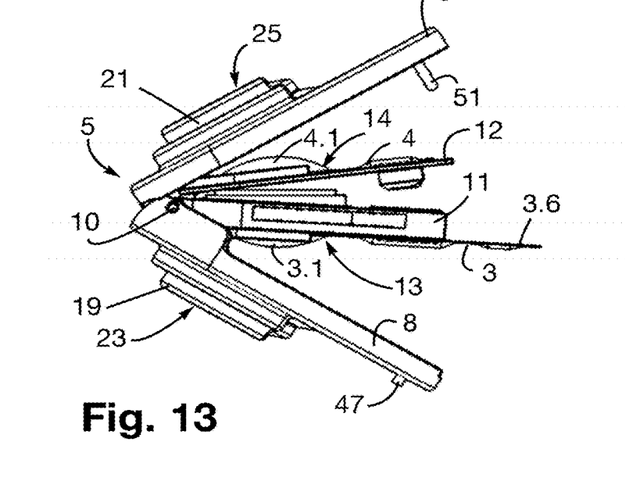
FIG. 13 is a side view of the receiving device of FIG. 7 equipped with the first and second capsules.
Figure 14:
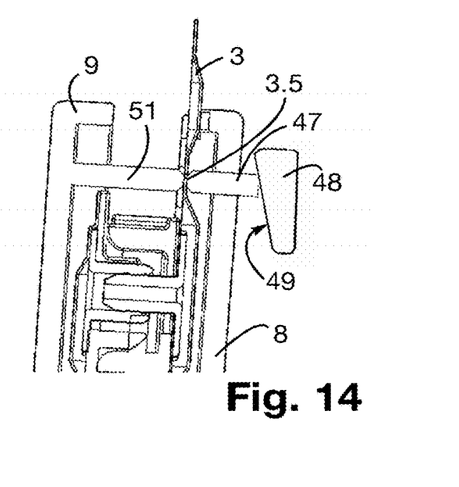
FIG. 14 is an enlarged view showing the cooperation of the first capsule with a counter-support element and a closure element provided on the receiving device.

As shown in FIGS. 7 and 13, the first capsule 3 is configured to extend partially outside the receiving device 5 when it is received in the receiving device 5 and the latter is in the closed position. Advantageously, the outlet orifice 3.6 is configured to extend outside the receiving device 5 when the first capsule 3 is received in the receiving device 5 and the latter is in the closed position.

Figure 9:
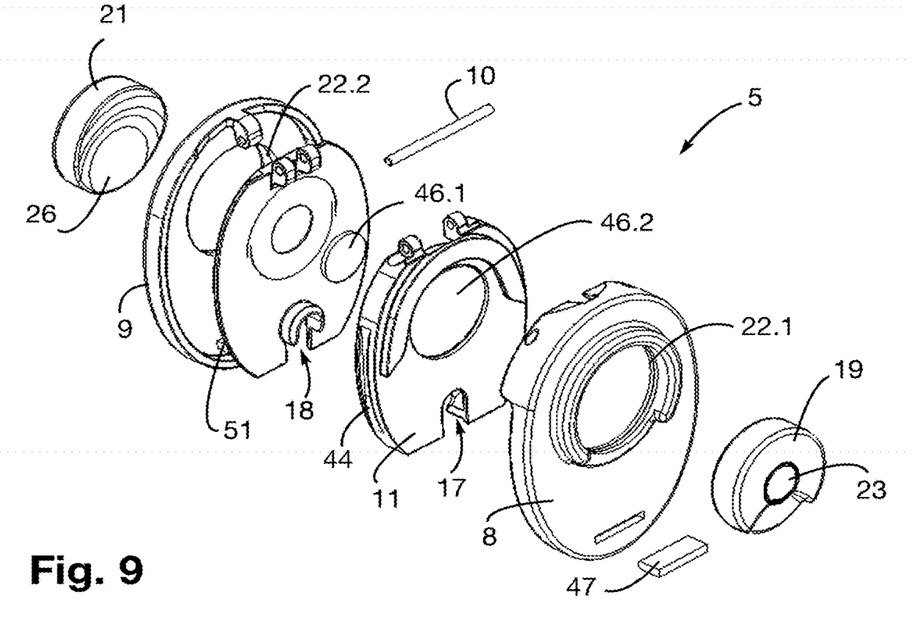
FIGS. 9 and 10 are exploded perspective views of the receiving device of FIG. 7.
Figure 10:
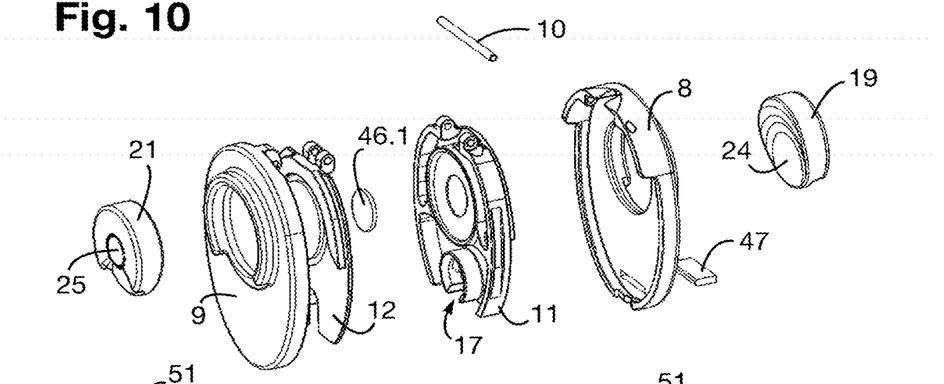
Figure 11:
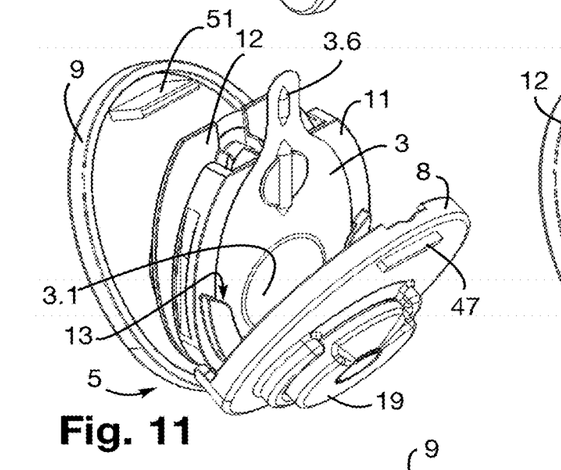
FIGS. 11 and 12 are perspective views of the receiving device of FIG. 7 equipped with the first and second capsules, showing first and second support portions respectively in an insertion position and in a connection position.
Figure 12:
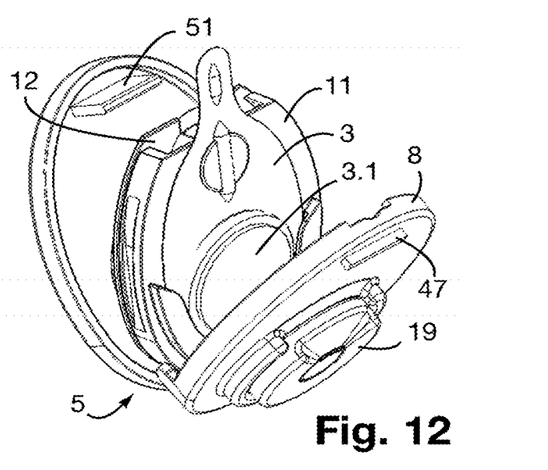
Figure 15:
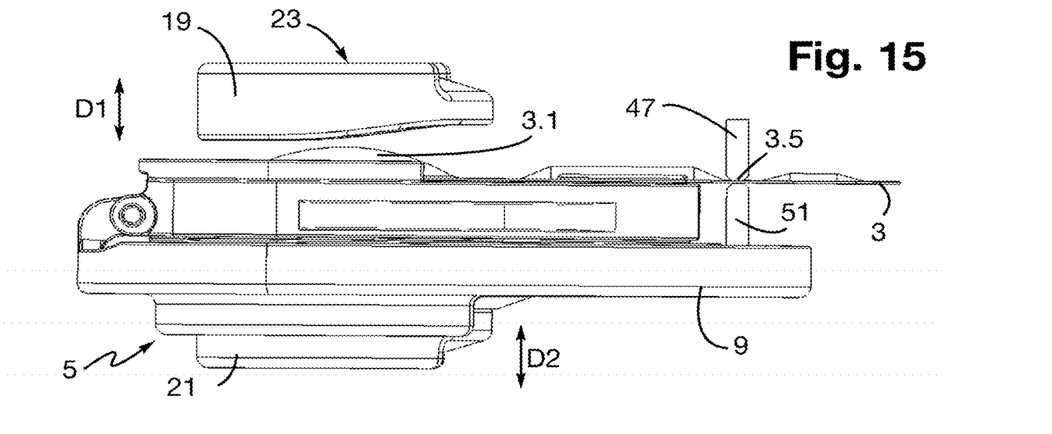
FIGS. 15 and 16 are partial side views of the receiving device of FIG. 7 equipped with the first and second capsules, showing a first bearing element respectively in an inactive position and in an active position.
Figure 16:
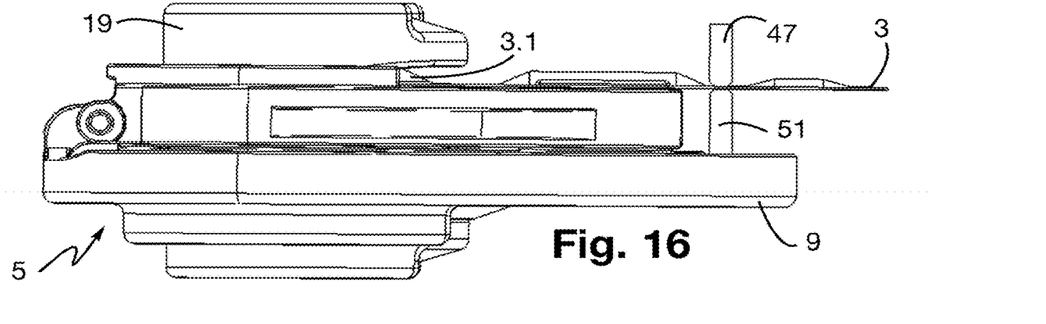
Figure 17:
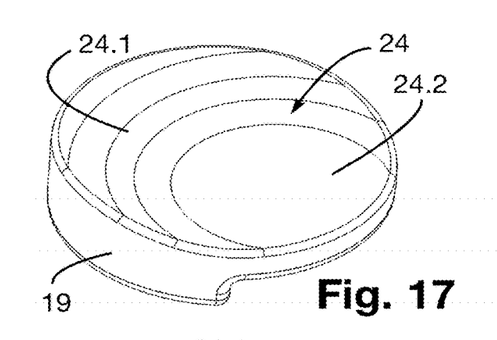
FIGS. 17 and 18 are perspective views respectively of the first and second bearing elements of the manufacturing apparatus.
Figure 18:
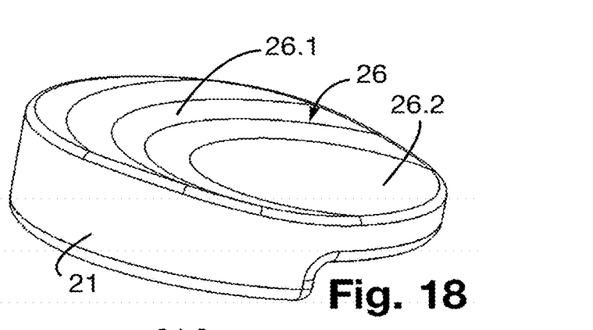
Figure 19:
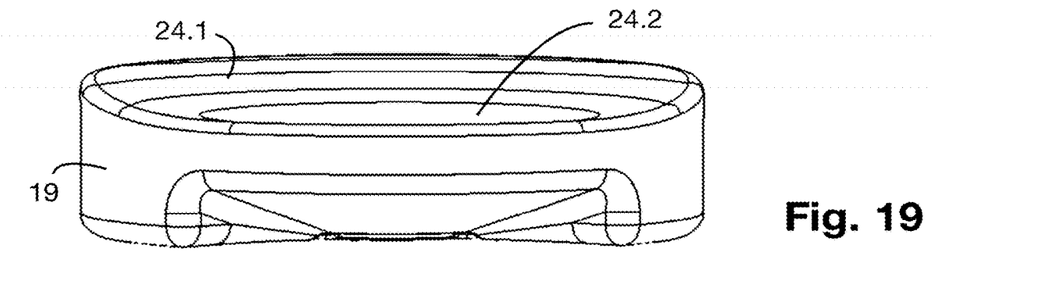
FIG. 19 is a front view of the first bearing element of the manufacturing apparatus.

As shown in particular in FIGS. 9, 15 and 16, the receiving device 5 further includes a first bearing element 19 configured to exert a pressing force on the first capsule 3, and more particularly on the first deformable compartment 3.1, and a second bearing element 21 configured to exert a pressing force on the second capsule 4, and more particularly on the second deformable compartment 4.1.

The first bearing element 19 is mounted on the first protecting shell 8 and is displaceable between an inactive position (see FIG. 15) and an active position (see FIG. 16) in which the first bearing element 19 is capable of exerting a pressing force on the first deformable compartment 3.1. For example, the first bearing element 19 may be mounted movable in translation along a first direction of displacement D1 which is transverse, and preferably substantially orthogonal, to the planes of extension of the first and second capsules 3, 4 when the receiving device 5 equipped with the first and second capsules 3, 4 is in the closed position.

According to the embodiment represented in FIGS. 1 to 22, the first bearing element 19 extends through a first passage opening 22.1 provided on the first protecting shell 8, and includes a first actuation surface 23 accessible from the outside of the receiving device 5, and more specifically from the outside of the receiving case 7. The function of the first actuation surface 23 will be defined later on.

The first bearing element 19 further includes a first bearing surface 24 opposite to the first actuation surface 23 and extending inside the receiving device 5. The first bearing surface 24 is configured to cooperate with the first deformable compartment 3.1, and to guide and orientate the content of the first capsule 3 toward the first connecting passage 3.3 of the first deformable compartment 3.1, when the first bearing element 19 exerts a pressing force on the first deformable compartment 3.1.

The first bearing surface 24 includes a first primary surface portion 24.1 configured to exert a pressing force on a first portion of the first deformable compartment 3.1, and a second primary surface portion 24.2 configured to exert a pressing force on a second portion of the first deformable compartment 3.1 which is closer to the first connecting passage 3.3 than the first portion of the first deformable compartment 3.1. According to the embodiment represented in FIGS. 1 to 22, the first primary surface portion 24.1 is configured to exert, on the first portion of the first deformable compartment 3.1, a pressing force which is orientated obliquely with respect to the first direction of displacement D1 and substantially toward the first connecting passage 3.3, and the second primary surface portion 24.2 is configured to exert, on the second portion of the first deformable compartment 3.1, a pressing force which is orientated substantially parallel to the first direction of displacement D1 or which is orientated obliquely with respect to the first direction of displacement and substantially toward the first connecting passage 3.3.

Advantageously, the first primary surface portion 24.1 is configured to exert a pressing force in particular on a rear portion of the first deformable compartment 3.1, that is to say a portion of the first deformable compartment 3.1 which is opposite to the first connecting passage 3.3, and the second primary surface portion 24.2 is configured to exert a pressing force in particular on a front portion of the first deformable compartment 3.1, that is to say a portion of the first deformable compartment 3.1 which is turned toward the first connecting passage 3.3.

According to the embodiment represented in FIGS. 1 to 22, the first primary surface portion 24.1 is formed by a protrusion, for example substantially arcuate, provided on the first bearing element 19, and the second primary surface portion 24.2 is substantially planar, and at least partially surrounded by the first primary surface portion 24.1.

More particularly, the first and second primary surface portions 24.1, 24.2 are configured such that, when the first bearing element 19 is displaced toward the active position, the first primary surface portion 24.1 exerts a pressing force on the first compartment 3.1 before the second primary surface portion 24.2 exerting a pressing force on the first compartment 3.1.

The second bearing element 21 being identical to the first bearing element 19, the structure and the operation of the second bearing element 21 are not described in details hereinafter for concision.

In particular, the second bearing element 21 extends through a second passage opening 22.2 provided on the second protecting shell 9, and includes a second actuation surface 25 accessible from the outside of the receiving case 7, and a second bearing surface 26 opposite to the second actuation surface 25. The second bearing surface 26 is configured to cooperate with the second deformable compartment 4.1, and to guide and orientate the content of the second capsule 4 toward the second connecting passage 4.3 of the second deformable compartment 4.1, when the second bearing element 21 exerts a pressing force on the second deformable compartment 4.1.

Advantageously, the second bearing surface 26 also includes first and second secondary surface portions 26.1, 26.2 configured such that, when the second bearing element 21 is displaced toward the active position, the first secondary surface portion 26.1 exerts a pressing force on the second compartment 4.1 before the second secondary surface portion 26.2 exerting a pressing force on the second compartment 4.1.

Advantageously, the first secondary surface portion 26.1 is configured to exert a pressing force in particular on a rear portion of the second deformable compartment 4.1, that is to say a portion of the second deformable compartment 4.1 which is opposite to the second connecting passage 4.3, and the second secondary surface portion 26.2 is particularly configured to exert a pressing force on a front portion of the second deformable compartment 4.1, that is to say a portion of the second deformable compartment 4.1 which is turned toward the second connecting passage 4.3.

Furthermore, like the first bearing element 19, the second bearing element 21 may also be mounted movable in translation along a second direction of displacement D2 which is transverse, and preferably substantially orthogonal, to the planes of extension of the first and second capsules 3, 4 when the receiving device 5 equipped with the first and second capsules 3, 4 is in the closed position.

For example, each of the first and second bearing elements 19, 21 may be made of a material which is at least partially deformable, and for example of silicone.

The receiving device 5 further includes a locking element (not represented in the figures), such as a locking pin, configured to lock the receiving device 5 in the closed position, and more particularly to lock the first and second protecting shells 8, 9 in the second position. Advantageously, the locking element is movable between a locking position in which the locking element locks the first and second protecting shells 8, 9 in the second position, and an unlocking position in which the locking element enables a displacement of the first and second protecting shells 8, 9 into the first position.

Advantageously, the receiving device 5 also includes a release element (not represented in the figures), such as a release button, configured to displace the locking element into the unlocking position. Advantageously, the release element is movable between an inactive position and an actuation position in which the release element is capable of displacing the locking element into the unlocking position.

Advantageously, the receiving device 5 includes a biasing element (not represented in the figures) configured to bias the release element into the inactive position.

Figure 20:
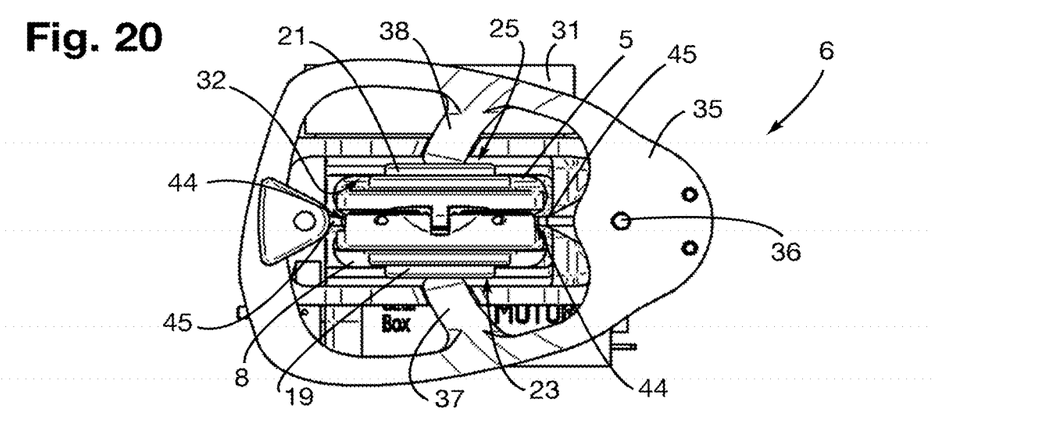
FIG. 20 is a partial top view of the manufacturing apparatus of FIG. 1.
Figure 21:
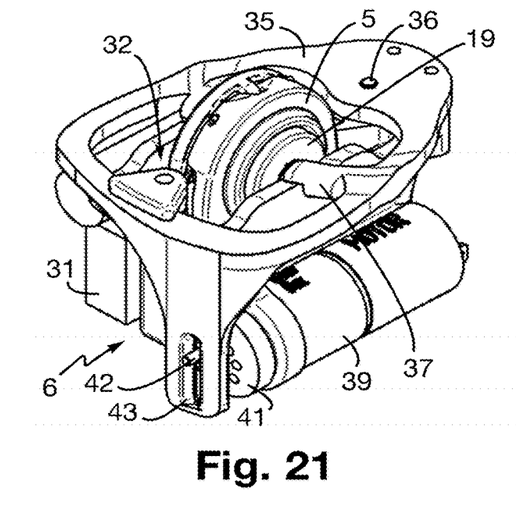
FIGS. 21 and 22 are partial perspective views of the manufacturing apparatus of FIG. 1.
Figure 22:
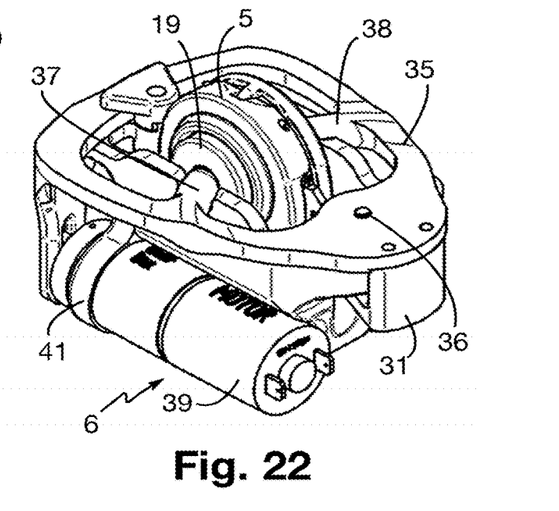

As shown more particularly in FIGS. 20 to 22, the mixing machine 6 includes a support 31, and a receiving housing 32 defined at least partially by the support 31 and configured to receive at least partially the receiving device 5. According to the embodiment represented in FIGS. 1 to 22, the mixing machine 6 and the receiving device 5 are configured such that the receiving device 5 extends at least partially outside the mixing machine 6, when the receiving device 5 is received in the receiving housing 32.

The mixing machine 6 also includes a base 33 in which the support 31 is housed, and an insertion opening 34 leading into the receiving housing 32, the receiving device 5 being configured to be inserted into the receiving housing 32 through the insertion opening 34. Advantageously, the insertion opening 34 is formed in a central portion of an upper surface of the base 33, and is configured to be orientated upwardly when the mixing machine 6 is disposed on a horizontal support surface.

The mixing machine 6 further includes an actuation portion 35 pivotally mounted on the support 31 about a substantially vertical pivot axis 36 when the mixing machine 6 is disposed on a horizontal support surface.

The actuation portion 35 includes a first actuation member 37, such as a first actuation pin, configured to transmit a pressing force to the first capsule 3, and a second actuation member 38, such as a second actuation pin, opposite to the first actuation member 37 and configured to transmit a pressing force to the second capsule 4. The first and second actuation members 37, 38 are configured to be disposed on either side of the receiving device 5 when the latter is received in the mixing machine 6, and more specifically in the receiving housing 32.

More particularly, the first and second actuation members 37, 38 are configured to exert pressing forces respectively and alternately on the first and second bearing elements 19, 21, so as to transmit pressing forces respectively and alternately on the first and second compartments 3.1, 4.1. In particular, the first and second actuation members 37, 38 are configured to cooperate respectively with the first and second actuation surfaces 23, 25 of the first and second bearing elements 19, 21.

According to the embodiment represented in FIGS. 1 to 22, the first and second actuation members 37, 38 extend substantially in the same plane of extension, and converge opposite to the pivot axis 36.

In addition, the mixing machine 6 includes a drive motor 39 mounted on the support 31. The drive motor 39 is configured to make the actuation portion 35 pivot about the pivot axis 36 and within a predetermined angular range.

According to the embodiment represented in FIGS. 1 to 22, the mixing machine 6 also includes a drive wheel 41 rotatably secured to an output shaft of the drive motor 39 and configured to be driven in rotation about its wheel axis and in a direction of rotation by the drive motor 39. The drive wheel 41 is equipped with a drive element 42, such as a drive pin, which is eccentric with respect to the wheel axis, and which is received in a receiving aperture 43 provided on the actuation portion 35. Advantageously, the receiving aperture 43 is elongate and extends in a direction of extension substantially parallel to the pivot axis 36. Such a configuration of the mixing machine 6 allows obtaining an alternating movement of the actuation portion 35 by making the drive motor 39 rotate always in the same direction of rotation, so that it is not necessary to resort to an expensive system for controlling the drive motor 39.

According to a variant of the invention, the mixing machine 6 may be configured such that a rotation of the drive motor 39 in a first direction of rotation causes a pivoting of the actuation portion 35 in a first pivot direction and a rotation of the drive motor 39 in a second direction of rotation, opposite to the first direction of rotation, causes a pivoting of the actuation portion 35 in a second pivot direction, opposite to the first pivot direction.

According to the embodiment represented in FIGS. 1 to 22, the receiving device 6 includes (see FIG. 20) two primary guide elements 44, such as guide grooves, configured to cooperate respectively with secondary guide elements 45, such as guide pins or guide legs, provided on the mixing machine 6, when the receiving device 5 is received in the mixing machine 6. The primary guide elements 44 may be provided for example on the first support portion 11, and the secondary guide elements 45 may be provided for example on the support 31. The presence of such guide elements allows facilitating the positioning of the receiving device 5 in the receiving housing 32.

The manufacturing apparatus 2 further includes a heating element 46 configured to heat up at least the first capsule 3 when the receiving device 5 equipped with the first and second capsules 3, 4 is received in the mixing machine 6. For example, the heating element 46 may comprise a heating resistor element 46.1 and a heating plate 46.2 adjacent to the heating resistor element 46.1.

According to an embodiment represented in the figures, the heating element 46 is disposed in the receiving device 5, and is advantageously mounted on the first support portion 11 so as to extend between the first and second capsules 3, 4 when these are received in the receiving device 5. Preferably, the heating element 46 is arranged so as to extend proximate to the first deformable compartment 3.1, and for example in contact with the first deformable compartment 3.1. However, according to another embodiment of the invention, the heating element 46 may be disposed in the mixing machine 6 and be configured to extend between the first and second capsules 3, 4 when the receiving device 5 equipped with the first and second capsules 3, 4 is received in the mixing machine 6.

According to an embodiment of the invention, the mixing machine 6 also includes an electric power supply source (not represented in the figures) configured to electrically power the mixing machine 6, and in particular the drive motor 39. For example, the electric power supply source may include at least one rechargeable battery.

Advantageously, when the heating element 46 is disposed in the receiving device 5, the electric power supply source is also configured to electrically power the receiving device 5, and in particular the heating element 46, when the receiving device 5 is received in the mixing machine 6. To this end, the mixing machine 6 includes a first electrical connector (not represented in the figures), and the receiving device 5 includes a second electrical connector (not represented in the figures) configured to be connected to the first electrical connector when the receiving device 5 is received in the mixing machine 6, so that the mixing machine 6 is capable of electrically powering the receiving device 5.

The mixing machine 6 further includes a controller, for example provided with a microcontroller, configured to control the operation of the drive motor 39 and of the heating element 46.

The manufacturing apparatus 2 further includes a closure element 47 configured to automatically close the outlet passage 3.5 of the first capsule 3 when the receiving device 5, equipped with the first and second capsules 3, 4, is received in the mixing machine 6, and to automatically clear the outlet passage 3.5 when the receiving device 5 equipped with the first and second capsules 3, 4 is removed out of the mixing machine 6. Advantageously, the closure element 47 is configured to exert a pressure on a wall of the outlet passage 3.5 so as to close the latter.

For example, the closure element 47 may be movably mounted on the first protecting shell 8 between a closing position (see FIGS. 14 and 15) in which the closure element 47 is capable of closing the outlet passage 3.5, and a clearance position (see FIG. 12) in which the closure element 47 is capable of clearing the outlet passage 3.5, and the mixing machine 6 may include for example a displacement element 48 configured to displace the closure element 47 into the closing position when the receiving device 5 is inserted into the mixing machine 6.

According to the embodiment represented in FIGS. 1 to 22, the displacement element 48 is fixedly mounted with respect to the support 31 and includes a displacement ramp 49 (see FIG. 14) configured to cooperate with the closure element 47 and displace the latter toward the clearance position.

Advantageously, the manufacturing apparatus 2 includes a biasing member (not represented in the figures) configured to bias the closure element 47 toward the clearance position. These arrangements ensure an automatic displacement of the closure element 47 into the clearance position as soon as the receiving device 5 is removed out of the mixing machine 6.

According to the embodiment represented in FIGS. 1 to 22, the manufacturing apparatus 2 further includes a counter-support element 51, such as a rib or a counter-support leg, configured to bear against the first capsule 3 and to be disposed opposite the closure element 47 when the receiving device 5 equipped with the first and second capsules 3, 4 is received in the mixing machine 6. Advantageously, the counter-support element 51 is provided on the receiving device 5, and for example on the second protecting shell 9. The presence of such a counter-support element ensures an optimum pinch of the outlet passage 3.5 when the receiving device 5 is received in the mixing machine 6.

A method for manufacturing a cosmetic product using the manufacturing apparatus 2 will now be described. In particular, such a manufacturing method comprises the following steps of:

providing the manufacturing apparatus 2,
displacing the first and second protecting shells 8, 9 into the first position,
displacing the first and second support portions 11, 12 into the receiving position,
inserting the first and second capsules 3, 4 respectively into the first and second receiving locations 13, 14,
displacing the first and second protecting shells 8, 9 into the second position so as to displace the first and second support portions 11, 12 into the connection position, and therefore so as to connect the first and second connection portions 3.2, 4.2,
inserting the receiving device 5 equipped with the first and second capsules 3, 4 into the receiving housing 32 of the mixing machine 6,
automatically displacing the closure element 47 into the closing position so as to automatically close the outlet passage 3.5 of the first capsule 3,
heating up the first deformable compartment 3.1 and the first formulation contained therein, and mixing the first and second formulations inside the first and second capsules 3, 4 so as to obtain the cosmetic product.

More particularly, the mixing step includes the following steps of:

making the actuation portion 35 pivot in the first pivot direction so that the first actuation member 37 exerts a pressing force on the first bearing element 19 and displaces the latter into the active position; such a displacement of the first bearing element 19 inducing an overpressure at the level of the first frangible peripheral area 3.10 of the first deformable compartment 3.1 and therefore a breakage of the respective frangible portion(s), then a flow of the first formulation, contained in the first deformable compartment 3.1, into the second buffer area 4.11 via the first connecting passage 3.3 and the second connecting passage 4.3; such a flow of the first formulation inducing an overpressure at the level of the second frangible peripheral area 4.10 of the second deformable compartment 4.1, and therefore a breakage of the respective frangible portion(s) and a penetration of the first formulation into the second deformable compartment 4.1, making the actuation portion 35 pivot in the second pivot direction so that the second actuation member 38 exerts a pressing force on the second bearing element 21, so as to displace the latter into the active position and induce a flow of the mixture of the first and second formulations contained in the second deformable compartment 4.1 into the first deformable compartment 3.1, and making the actuation portion 35 pivot successively in the first pivot direction and in the second pivot direction, and repeat such a step several times, and for example 2 to 15 times, advantageously 5 to 10 times, so as to make the mixture of the first and second formulations pass successively into the first deformable compartment 3.1 and into the second deformable compartment 4.1, in order to obtain a homogeneous mixture of the first and second formulations.

The manufacturing method further comprises the following steps of:

removing the receiving device 5 out of mixing machine 6, automatically displacing the closure element 47 into the clearance position so as to automatically clear the outlet passage 3.5 of the first capsule 3, manually exerting a mechanical pressure on the first and second bearing elements 19, 21 so as to expel the manufactured cosmetic product out of the first and second capsules 3, 4, and retrieving, for example on the fingers of a user, the manufactured cosmetic product.

Figure 23:
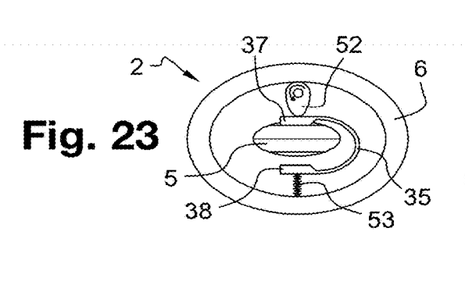
FIGS. 23 and 24 are schematic top views of a manufacturing apparatus according to a second embodiment of the invention.
Figure 24:
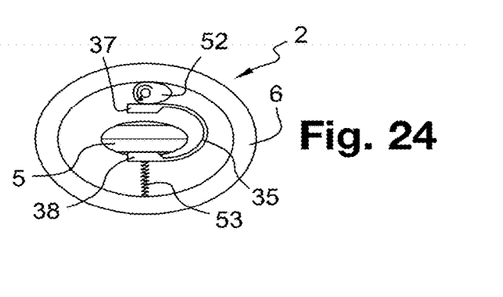

FIGS. 23 and 24 represent a manufacturing apparatus 2 according to a second embodiment of the invention which differs from that represented in FIGS. 1 to 22 in particular in that the actuation portion 35 is mounted movable in translation relative to the support 31 and is capable of occupying a first position in which the first actuation member 37 can exert a pressing force on the first bearing element 19 and a second position in which the second actuation member 38 can exert a pressing force on the second bearing element 21, and in that the mixing machine 6 includes a drive cam 52 rotatably secured to the drive motor 39 and configured to displace the actuation portion 35 toward the first position, and a biasing element 53, such as a helical spring, configured to bias the actuation portion 35 toward the second position.

It goes without saying that the invention is not limited to the sole embodiments of this manufacturing apparatus, described hereinabove as examples, but it comprises, on the contrary, all variants thereof. Thus, in particular, the first and second actuation members may be separate and distinct from each other.

The invention claimed is:

1. An apparatus for manufacturing a cosmetic product, comprising:
    a first capsule containing a predetermined amount of a first formulation, the first capsule including a first connection portion and an outlet passage provided with an outlet orifice,
    a second capsule containing a predetermined amount of a second formulation, and including a second connection portion configured to be connected to the first connection portion,
    a receiving device configured to receive the first and second capsules,
    a mixing machine configured to receive the receiving device equipped with the first and second capsules, and to mix the first and second formulations contained in the first and second capsules so as to obtain the cosmetic product,
    wherein the outlet passage is fluidly connected to the first connection portion, and wherein the manufacturing apparatus is configured to automatically close the outlet passage when the first and second capsules are received in the mixing machine, and to automatically clear the outlet passage when the first and second capsules are removed out of the mixing machine.

2. The manufacturing apparatus according to claim 1, wherein the receiving device is capable of occupying an open position in which the first and second capsules can be introduced into the receiving device, and a closed position in which the receiving device can hold the first and second capsules in position.

3. The manufacturing apparatus according to claim 2, wherein the receiving device is configured to fluidly connect the first and second connection portions when the receiving device is displaced into the closed position.

4. The manufacturing apparatus according to claim 1, wherein the first capsule includes a first deformable compartment containing the first formulation, and the second capsule includes a second deformable compartment containing the second formulation.

5. The manufacturing apparatus according to claim 4, wherein the first capsule further includes a first connecting passage configured to fluidly connect the first deformable compartment and the first connection portion, and the second capsule further includes a second connecting passage configured to fluidly connect the second deformable compartment and the second connection portion.

6. The manufacturing apparatus according to claim 5, wherein the outlet passage extends from and in line with the first connecting passage.

7. The manufacturing apparatus according to claim 5, wherein the first connection portion extends perpendicular with respect to the first connecting passage.

8. The manufacturing apparatus according to claim 1, further including a closure element configured to automatically close the outlet passage when the first and second capsules are received in the mixing machine, and to automatically clear the outlet passage when the first and second capsules are removed out of the mixing machine.

9. The manufacturing apparatus according to claim 8, wherein the closure element is configured to pinch the outlet passage or to exert a pressure on the outlet passage.

10. The manufacturing apparatus according to claim 9, wherein the closure element is movably mounted between a closing position in which the closure element is capable of closing the outlet passage, and a clearance position in which the closure element is capable of clearing the outlet passage.

11. The manufacturing apparatus according to claim 10, wherein the mixing machine includes a displacement element configured to displace the closure element into the closing position when the first and second capsules are received in the mixing machine.

12. The manufacturing apparatus according to claim 10, wherein the apparatus is configured such that introduction of the receiving device into the mixing machine up to an abutment position of the receiving device mechanically causes a displacement of the closure element into the closing position.

13. The manufacturing apparatus according to claim 10, wherein the apparatus is configured such that removal of the receiving device out of the mixing machine mechanically causes a displacement of the closure element into the clearance position.

14. The manufacturing apparatus according to claim 8, further comprising a counter-support element configured to bear against the first capsule and to be disposed opposite the closure element when the first and second capsules are received in the mixing machine.

15. The manufacturing apparatus according to claim 8, wherein the receiving device includes the closure element.

16. The manufacturing apparatus according to claim 1, wherein the first capsule includes a thermoformed shell and a sealing sheet covering the thermoformed shell, the thermoformed shell and the sealing sheet of the first capsule delimiting the outlet passage.

17. The manufacturing apparatus according to claim 1, wherein the mixing machine is configured to mix the first and second formulations inside the first and second capsules.

18. The manufacturing apparatus according to claim 1, further comprising a heating element configured to heat up at least one of the first and second capsules when the first and second capsules are received in the mixing machine.

19. The manufacturing apparatus according to claim 2, wherein the manufacturing apparatus is configured such that introduction of the receiving device into the mixing machine mechanically and automatically causes the closing of the outlet passage.

20. A method for manufacturing a cosmetic product, comprising the following steps of:
provided an apparatus for manufacturing a cosmetic product, the apparatus comprising: a first capsule containing a predetermined amount of a first formulation, the first capsule including a first connection portion and an outlet passage provided with an outlet orifice, a second capsule containing a predetermined amount of a second formulation, and including a second connection portion configured to be connected to the first connection portion, a receiving device configured to receive the first and second capsules, a mixing machine configured to receive the receiving device equipped with the first and second capsules, and to mix the first and second formulations contained in the first and second capsules so as to obtain the cosmetic product, wherein the outlet passage is fluidly connected to the first connection portion, and wherein the manufacturing apparatus is configured to automatically close the outlet passage when the first and second capsules are received in the mixing machine, and to automatically clear the outlet passage when the first and second capsules are removed out of the mixing machine,
manually inserting the first and second capsules into the mixing machine,
automatically closing the outlet passage,
automatically mixing the first and second formulations so as to obtain the cosmetic product,
manually removing the first and second capsules out of the mixing machine, and
automatically clearing the outlet passage.

21. An apparatus for manufacturing a cosmetic product, comprising:
a first capsule containing a predetermined amount of a first formulation, the first capsule including a first connection portion and an outlet passage provided with an outlet orifice, the outlet passage being fluidly connected to the first connection portion,
a second capsule containing a predetermined amount of a second formulation, and including a second connection portion configured to be connected to the first connection portion,
a mixing machine configured to receive the first and second capsules, and to mix the first and second formulations contained in the first and second capsules so as to obtain the cosmetic product,
a closure element configured to automatically close the outlet passage when the first and second capsules are received in the mixing machine, and to automatically clear the outlet passage when the first and second capsules are removed out of the mixing machine.

* * * * *